United States Patent
Kim et al.

(10) Patent No.: US 9,932,041 B2
(45) Date of Patent: Apr. 3, 2018

(54) PERSONALIZED MEDICAL EMERGENCY AUTOPILOT SYSTEM BASED ON PORTABLE MEDICAL DEVICE DATA

(71) Applicant: TOYOTA JIDOSHA KABUSHIKI KAISHA, Toyota-shi, Aichi-ken (JP)

(72) Inventors: BaekGyu Kim, Mountain View, CA (US); Chung-Wei Lin, Mountain View, CA (US); Shinichi Shiraishi, Mountain View, CA (US)

( * ) Notice: Subject to any disclaimer, the term of this patent is extended or adjusted under 35 U.S.C. 154(b) by 0 days.

(21) Appl. No.: 15/233,843

(22) Filed: Aug. 10, 2016

(65) Prior Publication Data

US 2018/0043901 A1   Feb. 15, 2018

(51) Int. Cl.
*B60W 40/08* (2012.01)
*G05D 1/00* (2006.01)
(Continued)

(52) U.S. Cl.
CPC ......... *B60W 40/08* (2013.01); *A61B 5/0024* (2013.01); *A61B 5/021* (2013.01); *A61B 5/024* (2013.01); *A61B 5/0205* (2013.01); *A61B 5/14532* (2013.01); *A61B 5/14551* (2013.01); *A61B 5/6801* (2013.01); *B60W 30/182* (2013.01); *G05D 1/0061* (2013.01); *G06F 19/323* (2013.01); *H04W 4/028* (2013.01);
(Continued)

(58) Field of Classification Search
CPC ............... B60W 40/08; B60W 30/182; B60W 2040/0872; B60W 2600/00; B60W 2040/0818; A61B 5/6801; A61B 5/14532; A61B 5/0024; A61B 5/021; A61B 5/024; A61B 5/14551; A61B 5/0205; G06F 19/323; H04W 4/046; H04W 4/028; H04W 4/22; G05D 1/0061
See application file for complete search history.

(56) References Cited

U.S. PATENT DOCUMENTS 8,725,311 B1 *  5/2014  Breed .................... G08B 21/06
                                                         600/300
9,616,899 B2 *  4/2017  Sprock ................. B60W 40/08
(Continued)

FOREIGN PATENT DOCUMENTS

JP    2015-133050    7/2015
JP    2016-009248    1/2016

*Primary Examiner* — Rodney A Butler
(74) *Attorney, Agent, or Firm* — Burbage Law, P.C.; Jon-Michael Burbage; Elizabeth Ruzich

(57) ABSTRACT

The disclosure includes implementations for providing a personalized medical emergency autopilot system based on data from a portable medical device. A method may include receiving, by a communication unit of a vehicle, a wireless message from a wireless network. The wireless message includes sensor data describing one or more current physiological signals of a driver of the vehicle that are recorded by a portable medical device worn by the driver. The method may include analyzing the one or more current physiological signals of the driver to identify a medical emergency for the driver. The method may include overriding, by a personalized medical emergency autopilot system, one or more vehicle control inputs provided by the driver subsequent to identifying the medical emergency so that the driver cannot control the operation of the vehicle during the medical emergency.

20 Claims, 7 Drawing Sheets

(51) Int. Cl.
*A61B 5/00*     (2006.01)
*H04W 4/02*     (2009.01)
*H04W 4/22*     (2009.01)
*H04W 4/04*     (2009.01)
*G06F 19/00*    (2018.01)
*B60W 30/182*   (2012.01)
*A61B 5/1455*   (2006.01)
*A61B 5/024*    (2006.01)
*A61B 5/021*    (2006.01)
*A61B 5/145*    (2006.01)
*A61B 5/0205*   (2006.01)

(52) U.S. Cl.
CPC ............ *H04W 4/046* (2013.01); *H04W 4/22* (2013.01); *B60W 2040/0818* (2013.01); *B60W 2040/0872* (2013.01); *B60W 2600/00* (2013.01)

(56) References Cited

U.S. PATENT DOCUMENTS

| | | | |
|---|---|---|---|
| 9,676,395 B2* | 6/2017 | Siddiqui | G06F 3/013 |
| 9,773,281 B1* | 9/2017 | Hanson | G06Q 40/08 |
| 2014/0276090 A1* | 9/2014 | Breed | A61B 5/18 600/473 |
| 2015/0219464 A1* | 8/2015 | Beaurepaire | G01C 21/3617 701/538 |
| 2017/0039084 A1* | 2/2017 | Atsmon | G06F 9/45558 |
| 2017/0249824 A1* | 8/2017 | Kaplan | G08B 21/06 |

\* cited by examiner

PERSONALIZED MEDICAL EMERGENCY AUTOPILOT SYSTEM BASED ON PORTABLE MEDICAL DEVICE DATA

BACKGROUND

The specification relates to a personalized medical emergency autopilot system based on data from a portable medical device.

Vehicles increasing include Advanced Driver Assistance Systems (herein an "ADAS system" if singular or "ADAS systems" if plural). ADAS systems may control some or all aspects of the operation of a vehicle.

Many car accidents occur due to unforeseen medical conditions of the drivers. For example, a driver experiences a sudden heart attack, a seizure, a stroke, a loss of consciousness or some other condition that results in the driver losing control of their vehicle and causing an accident.

Portable medical devices are increasing in popularity. These devices generate sensor data (which may be referred to as "physiological signals") that can be used to proactively identify when a driver is experiencing a risky medical condition that may result in an accident.

SUMMARY

Vehicle control systems would be capable of mitigating accidents caused by unforeseen medical conditions if they had access to the sensor data provided by portable medical devices. However, there is no technology currently available that integrates portable medical devices with a vehicle's ADAS system so that the ADAS system may access sensor data generated by the portable medical devices to prevent an accident caused by a driver's unforeseen medical condition. The personalized medical emergency autopilot system described herein solves this problem.

The personalized medical emergency autopilot system may integrate an ADAS system with one or more portable medical devices that a driver of the vehicle is wearing. Examples of portable medical devices may include pulse oximeters and heart rate monitors (e.g., both are common in smartwatches and other wearable computing devices) that can monitor the driver's physiological signal and provide sensor data to the ADAS that describes these physiological signals.

In some implementations, the personalized medical emergency autopilot system may remain inactive during normal driving conditions (e.g., when the physiological conditions to not indicate a medical emergency, this may be an example of "normal driving conditions"). However, when the personalized medical emergency autopilot system identifies sudden changes in the physiological signals of the drivers in an abnormal way, thereby indicating a medical emergency, the personalized medical emergency autopilot system may perform one or more of the following steps: (1) override any of the drivers' vehicle control inputs during the medical emergency (e.g., the driver's sudden braking, or the driver's sudden steering wheel rotation into a pedestrian road); (2) retrieve the driver's personalized emergency remedial action plan describing possible medical emergencies and how the personalized medical emergency autopilot system should respond to these medical emergencies if they occur; (3) determine what type of medical emergency the driver is experiencing; (4) determine how to respond to the medical emergency; and (5) take steps to respond to the medical emergency (e.g., automatically driving the vehicle to safe place while wirelessly calling for emergency medical assistance) while continuing to override and of the vehicle control inputs provided by the driver while the physiological signals continue to indicate the presence of a medical emergency.

Prior art ADAS systems always assign the driver's vehicle control inputs a higher priority than the vehicle control input of the ADAS system. For example, current ADAS systems assume that drivers are always capable of performing safer driving maneuvers than the ADAS system. By comparison, the personalized medical emergency autopilot system normally assumes that drivers are capable of performing safer driving maneuvers than the ADAS system, and therefore assigns a higher priority to their vehicle control inputs. However, from the moment a medical emergency is identified based on knowledge of the physiological signal directly measured from the driver's body in real time (or near real time) by a portable medical device, the personalized medical emergency autopilot system assumes that vehicle control inputs provided by the driver are unsafe or unreliable, and so, the personalized medical emergency autopilot system assigns a higher priority to the vehicle control inputs of the ADAS system. No other ADAS system provides this functionality in response to receiving physiological signals, directly measured from the driver's body in real time (or near real time) by a portable medical device, that indicate the presence of a medical emergency.

As described above, the personalized medical emergency autopilot system integrates physiological signals received from portable medical devices with a vehicle's ADAS system. The portable medical device may also provide the personalized medical emergency autopilot system with medical history data about the driver (for example: the driver's historical physiological readings as recorded by the personal medical device; the driver's height, the weight, gender, age, exercise habits; whether the driver is a smoker, etc.) that will beneficially enable the personalized medical emergency autopilot system to more accurately analyze the physiological signals received from the portable medical devices of the driver and correctly identify the presence of a medical emergency, possibly before the medical emergency even occurs. Prior art ADAS systems do not incorporate physiological signals that are directly measured from the body of the driver together with the medical history data of the driver into the ADAS system of a vehicle to provide a safer driver experience by identifying a medical emergency for the driver before or after it occurs.

The personalized medical emergency autopilot system may then instruct the ADAS system to take specified remedial action that is personalized for the type of medical condition that is identified by the personalized medical emergency autopilot system. Prior art ADAS systems do not provide this functionality based on physiological signals received from portable medical devices and user inputs specifying the driver's preferred response to specific medical emergencies.

The personalized medical emergency autopilot system also includes a novel layered architecture which is depicted in FIG. 4.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

One general aspect includes a system including: a vehicle communicatively coupled to a portable medical device of a driver via a wireless network; where the vehicle includes an ADAS system; where the ADAS system includes a personalized medical emergency autopilot system that is operable to receive sensor data of the driver via the wireless network, where the sensor data describes one or more current physiological signals describing the driver as recorded by one or more physiological sensors included in the portable medical device of the driver; where the personalized medical emergency autopilot system is operable to analyze the one or more current physiological signals of the driver to identify a medical emergency for the driver; and where the personalized medical emergency autopilot system is operable to override one or more vehicle control inputs provided by the driver subsequent to identifying the medical emergency so that the driver cannot control the operation of the vehicle during the medical emergency. Other embodiments of this aspect include corresponding computer systems, apparatus, and computer programs recorded on one or more computer storage devices, each configured to perform the actions of the methods.

Implementations may include one or more of the following features. The system where the personalized medical emergency autopilot system is operable to identify a response that is customized for the identified medical emergency and control an operation of the ADAS system so that the ADAS system controls an operation of the vehicle so that the response is implemented. The system where the response includes autonomously driving the vehicle to a specified location. The system where the specified location is a medical facility and the response further includes wirelessly communicating with the medical facility via the wireless network to provide the medical facility with a wireless message that identifies the driver and the medical emergency. The system where the wireless message further identifies one or more of an estimated time of arrival for the vehicle at the medical facility and a current geographic location of the vehicle. The system where the specified location is parking location. The system where the parking location includes one or more of a parking spot or a location in a breakdown lane. The system where the response further includes wirelessly communicating with an emergency responder (e.g., a police department, a fire department, a hospital, a medical transportation service such as an ambulance or a helicopter) via the wireless network to provide the emergency responder with a wireless message that identifies the driver, the medical emergency and a geographic location of the parking location. The system where the geographic location is accurate to within plus or minus substantially three meters. Implementations of the described techniques may include hardware, a method or process, or computer software on a computer-accessible medium.

One general aspect includes a method including: receiving, by a communication unit of a vehicle, a wireless message from a wireless network, where the wireless message includes sensor data describing one or more current physiological signals of a driver of the vehicle that are recorded by a portable medical device worn by the driver; analyzing the one or more current physiological signals of the driver to identify a medical emergency for the driver; and overriding, by a personalized medical emergency autopilot system, one or more vehicle control inputs provided by the driver subsequent to identifying the medical emergency so that the driver cannot control the operation of the vehicle during the medical emergency. Other embodiments of this aspect include corresponding computer systems, apparatus, and computer programs recorded on one or more computer storage devices, each configured to perform the actions of the methods.

Implementations may include one or more of the following features. The method where the one or more vehicle control inputs include steering the vehicle. The method where the one or more vehicle control inputs include accelerating the vehicle. The method where the one or more vehicle control inputs include breaking the vehicle. The method where overriding the one or more vehicle control inputs provided by the driver includes assigning a highest priority to one or more vehicle control inputs provided by an ADAS system of the vehicle so that the ADAS system may control the operation of the vehicle and the driver cannot control the operation of the vehicle. The method where the wireless message is received via a secured communication channel and the method further includes decrypting the wireless message. The method where the sensor data is incorporated into an ADAS system of the vehicle so that the ADAS system has access to physiological signals of the driver. Implementations of the described techniques may include hardware, a method or process, or computer software on a computer-accessible medium.

One general aspect includes a computer program product of a vehicle including a non-transitory memory storing computer-executable code that, when executed by a processor of the vehicle, causes the processor to: receive a wireless message from a wireless network, where the wireless message includes sensor data describing one or more current physiological signals of a driver of the vehicle that are recorded by a portable medical device worn by the driver; analyze the one or more current physiological signals of the driver to identify a medical emergency for the driver; and override one or more vehicle control inputs provided by the driver subsequent to identifying the medical emergency so that the driver cannot control the operation of the vehicle during the medical emergency. Other embodiments of this aspect include corresponding computer systems, apparatus, and computer programs recorded on one or more computer storage devices, each configured to perform the actions of the methods.

Implementations may include one or more of the following features. The computer program product where the wireless message is transmitted to the wireless network by the portable medical device. The computer program product where the wireless message is received in substantially real time relative to when the one or more current physiological signals are recorded by the portable medical device. The computer program product where the one or more current physiological signals are directly recorded by the portable medical device and not inferred by the vehicle or the portable medical device. Implementations of the described techniques may include hardware, a method or process, or computer software on a computer-accessible medium.

BRIEF DESCRIPTION OF THE DRAWINGS

The disclosure is illustrated by way of example, and not by way of limitation in the figures of the accompanying drawings in which like reference numerals are used to refer to similar elements.

DETAILED DESCRIPTION

Figure 1A:
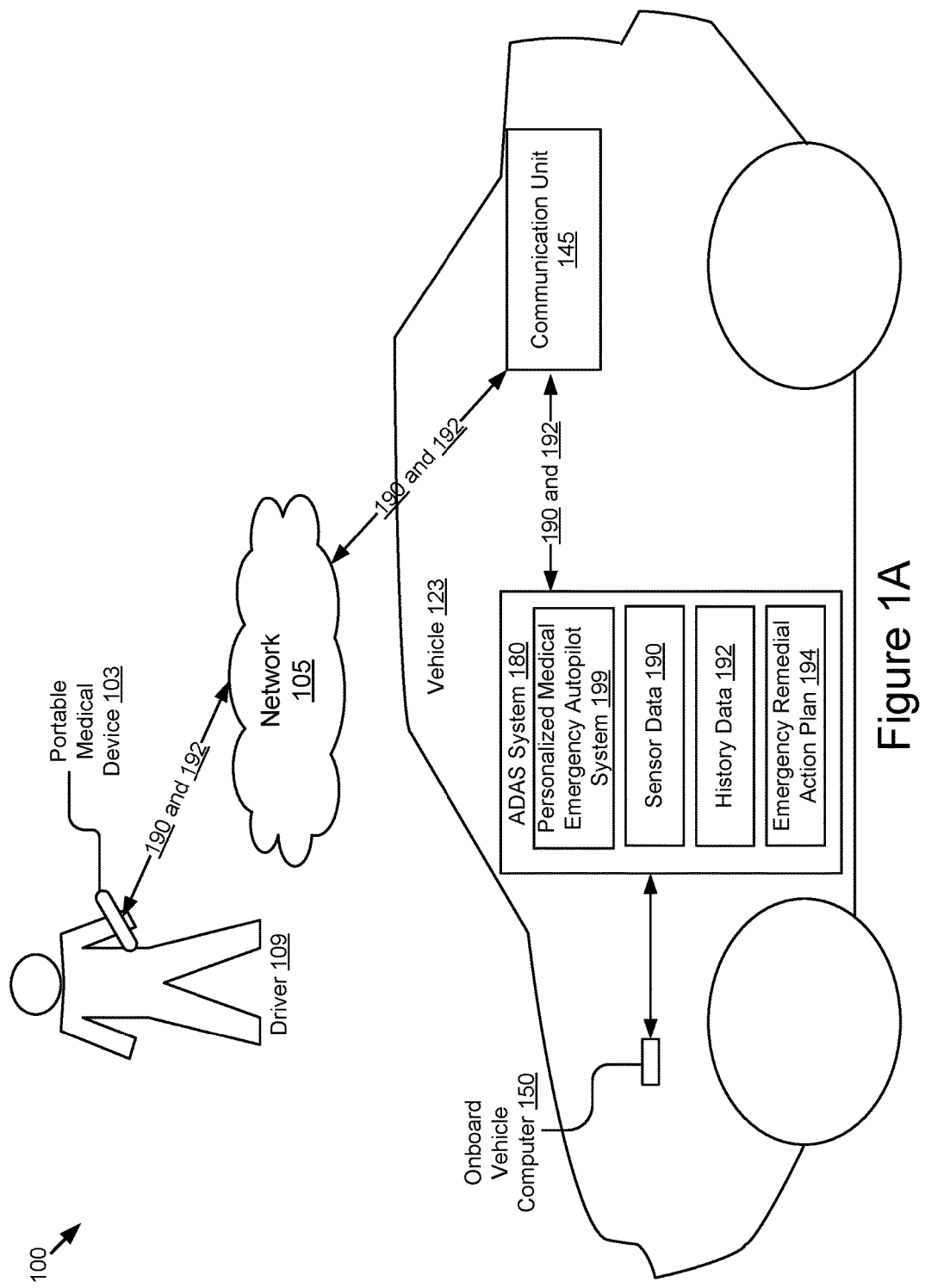
FIG. 1A is a block diagram illustrating an operating environment for a personalized medical emergency autopilot system according to some implementations.

An automotive system may include a vehicle. Vehicles increasingly include ADAS systems. An ADAS system may provide one or more safety features for a vehicle. For example, the ADAS system may control the operation of one or more vehicle functions in a way that is thought to make the vehicle operate more safely or conveniently for the driver.

Examples of ADAS systems include the following: an adaptive cruise control ("ACC") system; an adaptive high beam system; an adaptive light control system; an automatic parking system; an automotive night vision system; a blind spot monitor; a collision avoidance system; a crosswind stabilization system; a driver drowsiness detection system; a driver monitoring system; an emergency driver assistance system; a forward collision warning system; an intersection assistance system; an intelligent speed adaption system; a lane departure warning system; a pedestrian protection system; a traffic sign recognition system; a turning assistant; and a wrong-way driving warning system.

A vehicle may include a plurality of ADAS systems. These ADAS systems may provide a plurality of safety features.

The ADAS system may include a personalized medical emergency autopilot system. The personalized medical emergency autopilot system may control the operation of the ADAS system. The personalized medical emergency autopilot system may identify the presence of a medical emergency for a driver of the vehicle. The personalized medical emergency autopilot system may cause the vehicle to not respond to any vehicle control inputs provided by the driver during a medical emergency identified by the personalized medical emergency autopilot system. The personalized medical emergency autopilot system may instead prioritize the vehicle control inputs of the ADAS system over the vehicle control inputs of the driver (which may in fact be totally ignored as unreliable or unsafe). The personalized medical emergency autopilot system may include an emergency remedial action plan describing how the personalized medical emergency autopilot system should respond to specific medical emergencies or classes of medical emergencies. The personalized medical emergency autopilot system may cause the ADAS system to control the operation of the vehicle so that the vehicle behaves in a manner consistent with the emergency remedial action plan.

The vehicle may include one or more onboard vehicles computers. The onboard vehicle computer may execute or control the operation of the personalized medical emergency autopilot system.

An onboard vehicle computer may include a processor, a non-transitory storage medium storing computer code which may be accessed and executed by the processor and a communication unit which enables the vehicle to send and receive data via a wireless network (thereby making the vehicle a "connected vehicle"). In some implementations, the data received by the communication unit may include sensor data and history data transmitted to the wireless network by a portable medical device of the driver. The sensor data may describe the physiological signals of the driver. The history data may describe the medical history of the driver.

The one or more onboard vehicle computers may include one or more electronic control units ("ECU" if singular, "ECUs" if plural).

In some implementations, one or more of the ADAS systems may be provided by a virtual machine that virtualizes the operation of one or more hardware, software or firmware components to provide the functionality of ADAS systems in the real world. For example, the virtualization module may include one or more a hypervisor and a virtual machine monitor that is stored in a non-transitory memory of the safety system. A processor (e.g., a processor of an onboard vehicle computer or an ECU) may execute the hypervisor or the virtual machine monitor and, responsive to this execution, the hypervisor or the virtual machine monitor may cause the processor to create and run one or more virtual machines that provide virtualized hardware which are operable to provide a virtualized version of an ADAS system that provides one or more of the safety features described herein. In some implementations, for this virtualization, the same application can be deployed among different kinds of vehicle platforms as different virtual runtime platforms.

Referring now to FIG. 1A, depicted is a block diagram illustrating an operating environment 100 for a personalized medical emergency autopilot system 199 according to some implementations.

In some implementations, the operating environment 100 may include one or more of the following elements: the vehicle 123; and a portable medical device 103 of a driver 109. These elements may be communicatively coupled to a network 105.

The personalized medical emergency autopilot system 199 is described in more detail below with reference to FIGS. 1B-4. In some implementations, the operating environment 100 may include one or more personalized medical emergency autopilot systems 199. For example, the vehicle may include a plurality of ADAS systems 180 and two or more of these ADAS systems 180 may include a personalized medical emergency autopilot system 199.

The network 105 may be a conventional type, wired or wireless, and may have numerous different configurations including a star configuration, token ring configuration, or other configurations. Furthermore, the network 105 may include a local area network (LAN), a wide area network (WAN) (e.g., the Internet), or other interconnected data paths across which multiple devices and/or entities may communicate. In some implementations, the network 105 may include a peer-to-peer network. The network 105 may also be coupled to or may include portions of a telecommunications network for sending data in a variety of different communication protocols. In some implementations, the network 105 includes Bluetooth communication networks or a cellular communications network for sending and receiving data including via short messaging service (SMS), multimedia messaging service (MMS), hypertext transfer protocol (HTTP), direct data connection, wireless application protocol (WAP), e-mail, DSRC, full-duplex wireless communication, etc. The network 105 may also include a mobile data network that may include third-generation (3G), fourth-generation (4G), long-term evolution (LTE), Voice-over-LTE ("VoLTE") or any other mobile data network or combination of mobile data networks. Further, the network 105 may include one or more IEEE 802.11 wireless networks.

In some implementations, the network 105 may include one or more communication channels shared among the vehicle 123 and one or more other wireless communication devices. The communication channel may include DSRC, a full-duplex wireless communication (as described in U.S. patent application Ser. No. 14/471,387 filed on Aug. 28, 2014 and entitled "Full-Duplex Coordination System," the entirety of which is hereby incorporated by reference) or any other wireless communication protocol. For example, the network 105 may be used to transmit a full-duplex wireless message, a DSRC message, a DSRC probe or basic safety message among two or more of the elements of the operating environment 100.

The portable medical device 103 may include a processor-based computing device of the driver 109. The portable medical device 103 may include one or more physiological sensors for measuring physiological information of the driver 109. The portable medical device 103 may include any portable medical device that includes the necessary physiological sensors for recording sensor data 190 describing one or more physiological signals of the driver 109 and a wireless communication device (similar to the communication unit 145) that is operable to wirelessly transmit the sensor data 190 (as well as the history data 192 in some implementations) to the vehicle 123 via the network 105. For example, the portable medical device 103 may include a smartwatch or a fitness tracker (e.g., Fitbit). The portable medical device 103 may include a processor (similar to the processor 225 described below with reference to FIG. 2), a non-transitory memory (similar to the memory 227 described below with reference to FIG. 2), one or more physiological sensors and hardware or software configured to enable the portable medical device 103 to communicate with the network 105 (similar to the communication unit 145 described below).

The physiological sensors of the portable medical device 103 may include one or more of the following: a pulse oximeter; a heart rate monitor; a blood pressure cuff; a glucometer; and any other sensor or combination of sensors that are included in a portable medical device 103 and operable to measure a physiological signal or biological measurement of the driver 109.

The non-transitory memory of the portable medical device 103 may store the sensor data 190 and history data 192. The sensor data 190 may describe the physiological signals of the driver 109 that are recorded by the physiological sensors of the portable medical device 103. The history data 192 may describe a medical history of the driver 109. For example, the history data 192 may describe one or more of the following: historical physiological readings of the driver 109 as recorded by the portable medical device 103; a height of the driver 109; a weight of the driver 109; a birth gender of the driver 109; a race or ethnicity of the driver 109; an age of the driver 109; exercise habits of the driver 109 as recorded by the portable medical device 103; dietary preferences of the driver 109; whether the driver 109 is a smoker, medical insurance information of the driver 109 including their policy number and insurance provider, etc. Some of the history data 192 may be part of a user profile established by the driver 109 that describes certain static facts about the driver 109 such as their date of birth or gender at birth. Some aspects of the user profile may be dynamic and modified by other medical devices of the driver such as a smart scale that updates the weight of the driver 109 as it changes from day-to-day, week-to-week or some other time rate.

The communication unit of the portable medical device 103 may wirelessly transmit one or more of the sensor data 190 and the history data 192 to the network 105. The communication unit 145 of the vehicle 123 may receive the sensor data 190 and the history data 192 from the network 105 for provision to the personalized medical emergency autopilot system 199 of the ADAS system 180. This information may be repeatedly transmitted to the network 105 in real time or substantially real time so that the personalized medical emergency autopilot system 199 may have updated information which it may use to provide its functionality. The sensor data 190 and the history data 192 may be transmitted to the network 105 at the same time or at different times. For example, in some implementations the personalized medical emergency autopilot system 199 may receive the history data 192 at a lower rate than the sensor data 190. The personalized medical emergency autopilot system 199 may store the history data 192 in a cache or some other memory for repeated use.

In some implementations, the transmission of the sensor data 190 and the history data 192 to the communication unit 145 may be secured in order to keep this information confidential. For example, one or more of the sensor data 190 and the history data 192 may be encrypted and the personalized medical emergency autopilot system 199 may include an encryption key for decrypting this data. In some implementations, a secure VPN tunnel may be used to transmit one or more of the sensor data 190 and the history data 192. Other forms of secured transmission are possible, and those described here are intended to be illustrative and not limiting.

The portable medical device 103 may be paired with the communication unit 145 of the vehicle 123 so that the portable medical device 103 transmits data to the communication unit 145.

The driver 109 may include a human user of the portable medical device 103 or the vehicle 123.

The vehicle 123 may include a car, a truck, a sports utility vehicle, a bus, a semi-truck, a drone or any other roadway-based conveyance that includes a communication unit 145 and an ADAS system 180 having a personalized medical emergency autopilot system 199. In some implementations, the vehicle 123 may include an autonomous vehicle or a semi-autonomous vehicle. For example, the ADAS system 180 (or a plurality of ADAS systems 180) may render the vehicle 123 autonomous or semi-autonomous.

The vehicle 123 may include one or more of the following elements: a communication unit 145; a ADAS system 180 including a personalized medical emergency autopilot system 199; and an onboard vehicle computer 150. These elements may be communicatively coupled to one another via one or more busses in series (as pictured) or in parallel. The wireless coupling depicted in FIG. 1A is intended to be illustrative and not limiting.

The communication unit 145 may include hardware that transmits and receives data to and from the network 105. In some implementations, the communication unit 145 includes a port for direct physical connection to the network 105 or to another communication channel. For example, the communication unit 145 includes a USB, SD, CAT-5, or similar port for wired communication with the network 105. In some implementations, the communication unit 145 includes a wireless transceiver for exchanging data with the network 105 or other communication channels using one or more wireless communication methods, including IEEE 802.11, IEEE 802.16, Bluetooth, or another suitable wireless communication method.

In some implementations, the communication unit 145 includes a port for direct physical connection to the network 105 or to another communication channel. For example, the communication unit 145 includes a USB, SD, CAT-5, or similar port for wired communication with the network 105.

In some implementations, the communication unit 145 includes a wireless transceiver for exchanging data with the network 105 or other communication channels using one or more wireless communication methods, including: IEEE 802.11; IEEE 802.16, Bluetooth; EN ISO 14906:2004 Electronic Fee Collection—Application interface EN 12253:2004 Dedicated Short-Range Communication—Physical layer using microwave at 5.8 GHz (review); EN 12795:2002 Dedicated Short-Range Communication (DSRC)—DSRC Data link layer: Medium Access and Logical Link Control (review); EN 12834:2002 Dedicated Short-Range Communication—Application layer (review); EN 13372:2004 Dedicated Short-Range Communication (DSRC)—DSRC profiles for RTTT applications (review); the communication method described in U.S. patent application Ser. No. 14/471,387 filed on Aug. 28, 2014 and entitled "Full-Duplex Coordination System"; or another suitable wireless communication method.

In some implementations, the communication unit 145 may include a full-duplex coordination system as described in U.S. patent application Ser. No. 14/471,387 filed on Aug. 28, 2014 and entitled "Full-Duplex Coordination System."

In some implementations, the communication unit 145 includes a cellular communications transceiver for sending and receiving data over a cellular communications network including via short messaging service (SMS), multimedia messaging service (MMS), hypertext transfer protocol (HTTP), direct data connection, WAP, e-mail, or another suitable type of electronic communication. In some implementations, the communication unit 145 includes a wired port and a wireless transceiver. The communication unit 145 also provides other conventional connections to the network 105 for distribution of files or media objects using standard network protocols including TCP/IP, HTTP, HTTPS, and SMTP, millimeter wave, DSRC, etc.

The onboard vehicle computer 150 may include a special-purpose processor-based computing device of the vehicle 123. In some implementations, the onboard vehicle computer 150 may include an ECU. The onboard vehicle computer 150 may be an element of the ADAS 180 or it may be operable to execute the ADAS 180 or control the operation of the ADAS 180.

The onboard vehicle computer 150 may include a processor (similar to the processor 225 described below with reference to FIG. 2) and a non-transitory memory (similar to the memory 227 described below with reference to FIG. 2). The non-transitory memory may store one or more of the following: the sensor data 190; the history data 192; the emergency remedial action plan 194; and the personalized medical emergency autopilot system 199.

The ADAS system 180 may include one or more of the following: an adaptive cruise control system; an adaptive high beam system; an adaptive light control system; an automatic parking system; an automotive night vision system; a blind spot monitor; a collision avoidance system; a crosswind stabilization system; a driver drowsiness detection system; a driver monitoring system; an emergency driver assistance system; a forward collision warning system; an intersection assistance system; an intelligent speed adaption system; a lane departure warning system; a pedestrian protection system; a traffic sign recognition system; a turning assistant; a pre-crash safety system; and a wrong-way driving warning system.

In some implementations, the ADAS system 180 may be virtualized. For example, the ADAS system 180 may include one or more hypervisors. Alternatively, or in addition, the ADAS system 180 may include one or more virtual machine monitors. The one or more hypervisors and/or the one or more virtual machine monitors may be stored in a non-transitory memory of the onboard vehicle computer 150 or the vehicle 123. A processor of the onboard vehicle computer 150 or the vehicle 123 may execute a hypervisor or a virtual machine monitor and, responsive to this execution, the hypervisor or the virtual machine monitor may cause the processor to create and run one or more virtual machines that provide virtualized hardware which is operable to provide one or more of the safety features described herein.

The ADAS system 180 may provide a plurality of safety features. The safety features provided by the ADAS system 180 may include one or more of the following: adaptive cruise control for the vehicle 123 such as provided by an adaptive cruise control system; adaptive high beams for the vehicle 123 such as provided by an adaptive high beam system; adaptive lights for the vehicle 123 such as provided by an adaptive light control system; automatic or semi-automatic vehicle parking for the vehicle 123 such as provided by an automatic parking system; night vision for the vehicle 123 such as provided by an automotive night vision system; blind spot monitoring, detection and notification for the vehicle 123 such as provided by a blind spot monitor; risk of collision monitoring for the vehicle 123, risk of collision detection for the vehicle 123, risk of collision notification for the vehicle 123 and temporary automated driving of the vehicle 123 to avoid a collision such as provided a collision avoidance system, a forward collision warning system. a pedestrian protection system or a pre-crash safety system; crosswind monitoring, crosswind detection and crosswind stabilization for the vehicle 123 such as provided by a crosswind stabilization system; driver drowsiness monitoring, driver drowsiness detection and automated driving or braking of the vehicle 123 such as provided by a driver drowsiness detection system; monitoring of driver attentiveness, detection of driver lack of attentiveness detection, notification of driver regarding a safety risk relating to their lack of attentiveness and automated driving or braking of the vehicle 123 such as provided by a driver monitoring system; monitoring of driver behavior, detection of driver behavior associated with a safety risk, notification of driver regarding a safety risk relating to their behavior and automated driving or braking of the vehicle 123 such as provided by an emergency driver assistance system; monitoring of traffic at an intersection or in an oncoming lane or traffic, detection of a risk of collision at the intersection or by turning into the oncoming lane of traffic, notifying the driver of the risk of collision and automated driving or braking of the vehicle 123 to reduce the risk or collision or avoid an impending collision such as provided by an intersection assistance system or a turning assistant; ensuring that the speed of the vehicle 123 does not exceed a safe or legally enforced speed such as provided by an intelligent speed adaption system; warning the driver of the vehicle 123 when the vehicle begins to move out of its lane (unless a turn signal is on in that direction) such as provided by a lane departure warning system; traffic sign detection, driver notification of non-compliance or risk of non-compliance and automated or semi-automated driving or braking of the vehicle 123 to ensure compliance with the traffic sign such as provided by a traffic sign recognition system; monitoring of whether the vehicle 123 is driving in the wrong lane, notification to the driver of an event where the driver is driving in the wrong lane and automated driving or braking of the vehicle 123 to avoid a collision or correct a heading of the vehicle 123 to conform with the flow of traffic such as provided by a wrong-way driving warning system.

The ADAS system 180 may include or be communicatively coupled to a non-transitory memory that stores one or more of the following: the personalized medical emergency autopilot system 199; the sensor data 190; the history data 192; and the emergency remedial action plan 194.

The sensor data 190 and the history data 192 are those transmitted by the portable medical device 103. The personalized medical emergency autopilot system 199 may receive one or more of the sensor data 190 and the history data 192. The personalized medical emergency autopilot system 199 may incorporate this data with the other data considered by the ADAS system 180. The personalized medical emergency autopilot system 199 may analyze one or more of the sensor data 190 and the history data 192 to identify a combination of physiological information (described by the sensor data 190) for a predetermined period of time that correspond to a particular medical emergency for this particular driver 109 (based on the history data 192 for the driver 109).

In some implementations, the emergency remedial action plan 194 may include data describing how the personalized medical emergency autopilot system 199 should respond to an identified medical emergency (based, for example, on user input provided to the personalized medical emergency autopilot system 199 from the driver 109 or a medical professional such as a doctor or nurse). For example, the emergency remedial action plan 194 may include a table (or some other data structure) describing a list of medical emergencies in one column and an ordered list of responses in another column. For example, if the medical emergency identified by the personalized medical emergency autopilot system 199 is "heart attack," then the response may be to automatically and proactively, without need for input from the driver 109, cause one or more ADAS systems 180 of the vehicle 123 to complete one or more of the following tasks: (1) drive the vehicle 123 into the breakdown lane of the roadway (the vehicle 123 may include sensors to safely accomplish this task such as external cameras), (2) turn the vehicle 123 off, (3) determine the GPS coordinates of the vehicle 123 via a navigation system of the vehicle 123, (4) automatically communicate with emergency medical responders (by phone, text message, etc., such as provided by the communication unit 145) by providing the following information to the emergency medical responders: (a) identifying information of the driver 109 (name, gender, height, weight, age, insurance information); (b) the GPS coordinates for the vehicle; and (c) the medical emergency identified by the personalized medical emergency autopilot system 199.

Other action plans are possible for different situations. For example, if the vehicle 123 is autonomous, then the response may be for the vehicle 123 to identify the nearest hospital, autonomously drive to the nearest hospital and, while still in route, contact the hospital to inform them of the following information: (a) identifying information of the driver (name, gender, height, weight, age, insurance information); and (b) the medical emergency identified by the personalized medical emergency autopilot system 199.

In some implementations, the personalized medical emergency autopilot system 199 may include code and routines that are operable, when executed by a processor, to cause the processor to perform one or more of the steps of the method 300 described below with reference to FIGS. 3A and 3B.

The personalized medical emergency autopilot system 199 may include a thin client that is executed by a processor-based computing system of the vehicle 123 such as the onboard vehicle computer 150 or the ADAS system 180.

In some implementations, the personalized medical emergency autopilot system 199 may be implemented using hardware including a field-programmable gate array ("FPGA") or an application-specific integrated circuit ("ASIC"). In some other implementations, the personalized medical emergency autopilot system 199 may be implemented using a combination of hardware and software. The personalized medical emergency autopilot system 199 may be stored in a combination of the devices (e.g., servers or other devices), or in one of the devices.

In some implementations, the vehicle 123 may include a sensor set. The sensor set may include one or more sensors. The sensor set may collect readings describing the physical environment of the vehicle 123 or the physical environment internal to the vehicle 123 where the driver 109 is located. The ADAS system 180 may modify the operation of the vehicle 123 or control the operation of the vehicle 123 based in part on the readings of the sensor set and the instructions provided by the personalized medical emergency autopilot system 199.

In some implementations, the one or more physical characteristics measured by the sensor set of the vehicle 123 may be recorded directly (e.g., atmospheric pressure, temperature, or any other parameters capable of direct measurement by a vehicle sensor) or indirectly (e.g., an image or sound recording that depicts or describes a physical characteristic of the physical environment or an object or event present within the physical environment).

In some implementations, the sensor set may include one or more sensors that are operable to measuring the performance of the vehicle 123. For example, the sensor set may record data that describes a speed or acceleration of the vehicle 123.

In some implementations, the sensor set of the vehicle 123 may include one or more of the following vehicle sensors: an external microphone; an internal microphone; an external camera; an internal camera; a LIDAR sensor; a laser altimeter; a navigation sensor (e.g., a global positioning system sensor of the DSRC-compliant GPS unit that is accurate to within 1.5 meters, as opposed to being accurate to within 10 meters as is the case for non-DSRC-compliant GPS units); an infrared detector; a motion detector; a thermostat; a sound detector, a carbon monoxide sensor; a carbon dioxide sensor; an oxygen sensor; a mass air flow sensor; an engine coolant temperature sensor; a throttle position sensor; a crank shaft position sensor; an automobile engine sensor; a valve timer; an air-fuel ratio meter; a blind spot meter; a curb feeler; a defect detector; a Hall effect sensor, a manifold absolute pressure sensor; a parking sensor; a radar gun; a speedometer; a speed sensor; a tire-pressure monitoring sensor; a torque sensor; a transmission fluid temperature sensor; a turbine speed sensor (TSS); a variable reluctance sensor; a vehicle speed sensor (VSS); a water sensor; a wheel speed sensor; and any other type of automotive sensor.

The sensor set may be operable to record data that describes one or more locations of the vehicle 123 at one or more different times, images or other measurements of the vehicle environment and objects or other vehicles present in the vehicle environment where the vehicle 123 is located, etc. The vehicle environment may include the area outside of the vehicle 123 that is proximate to the vehicle 123. For example, the vehicle 123 may be in motion on a roadway and the vehicle environment may include other vehicles that are in front of the vehicle 123, behind the vehicle 123, beside the vehicle 123 or one or more car lengths away from the vehicle 123.

In some implementations that vehicle 123 may include a panel that may depict a message that describes the identified medical emergency and the steps that are being taken to remedy the emergency. The panel may include an electronic display panel or monitor of the vehicle 123. For example, the panel may include an electronic display panel of a head-unit or heads-up display unit of the vehicle 123.

The heads-up display unit may include a three-dimensional heads-up display unit such as the one described in U.S. patent application Ser. No. 15/080,433 filed on Mar. 24, 2016 and entitled "Wireless Data Sharing Between a Mobile Client Device and a Three-Dimensional Heads-Up Display Unit," the entirety of which is herein incorporated by reference.

Figure 1B:
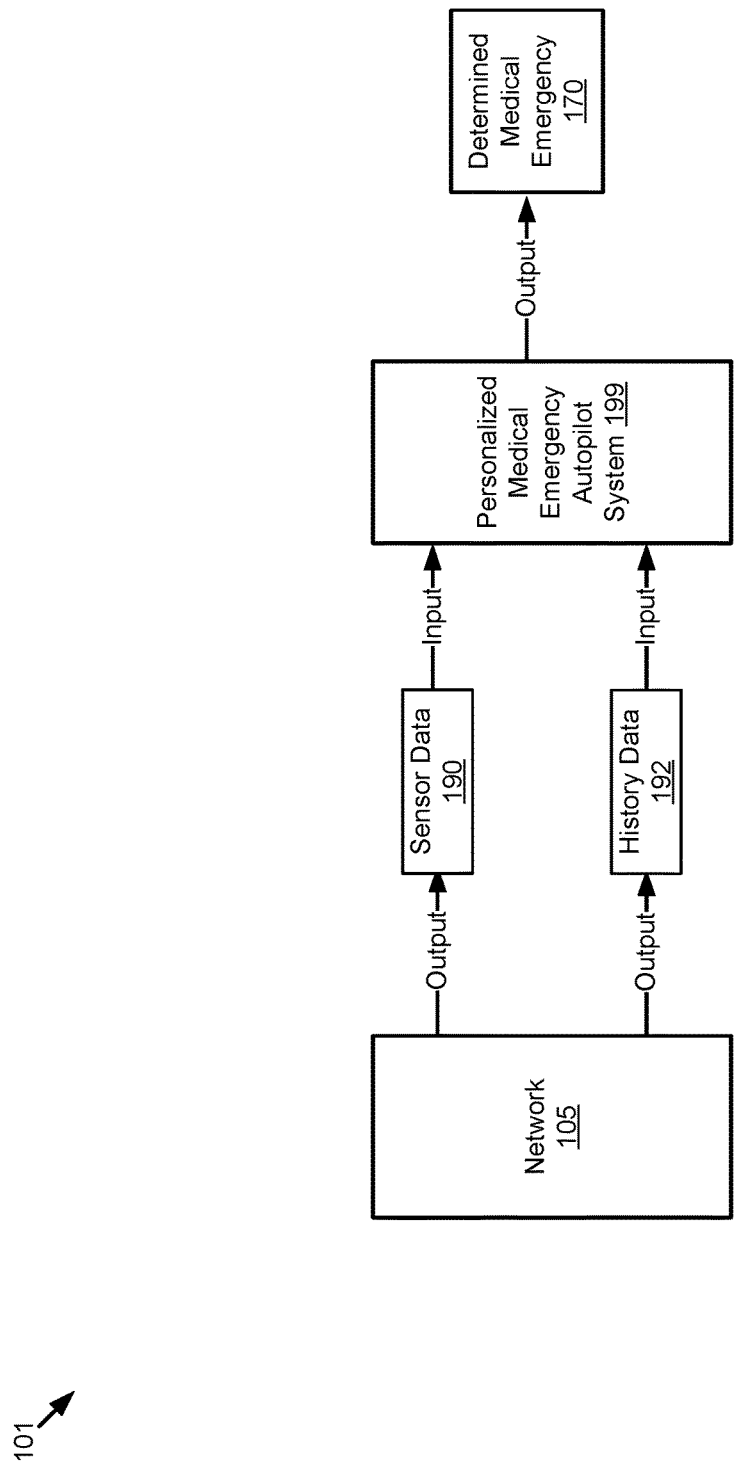
FIG. 1B is a block diagram illustrating process flow for a personalized medical emergency autopilot system according to some implementations.

Referring now to FIG. 1B, depicted is a block diagram illustrating process flow 101 for the personalized medical emergency autopilot system 199 according to some implementations.

The network 105 may output the sensor data 190 and the history data 192. The personalized medical emergency autopilot system 199 may receive the sensor data 190 and the history data 192 as an input. The personalized medical emergency autopilot system 199 may analyze the sensor data 190 and the history data 192. The personalized medical emergency autopilot system 199 may provide an output based on the sensor data 190 and the history data 192. The output may include a determination of a medical emergency 170.

Figure 1C:
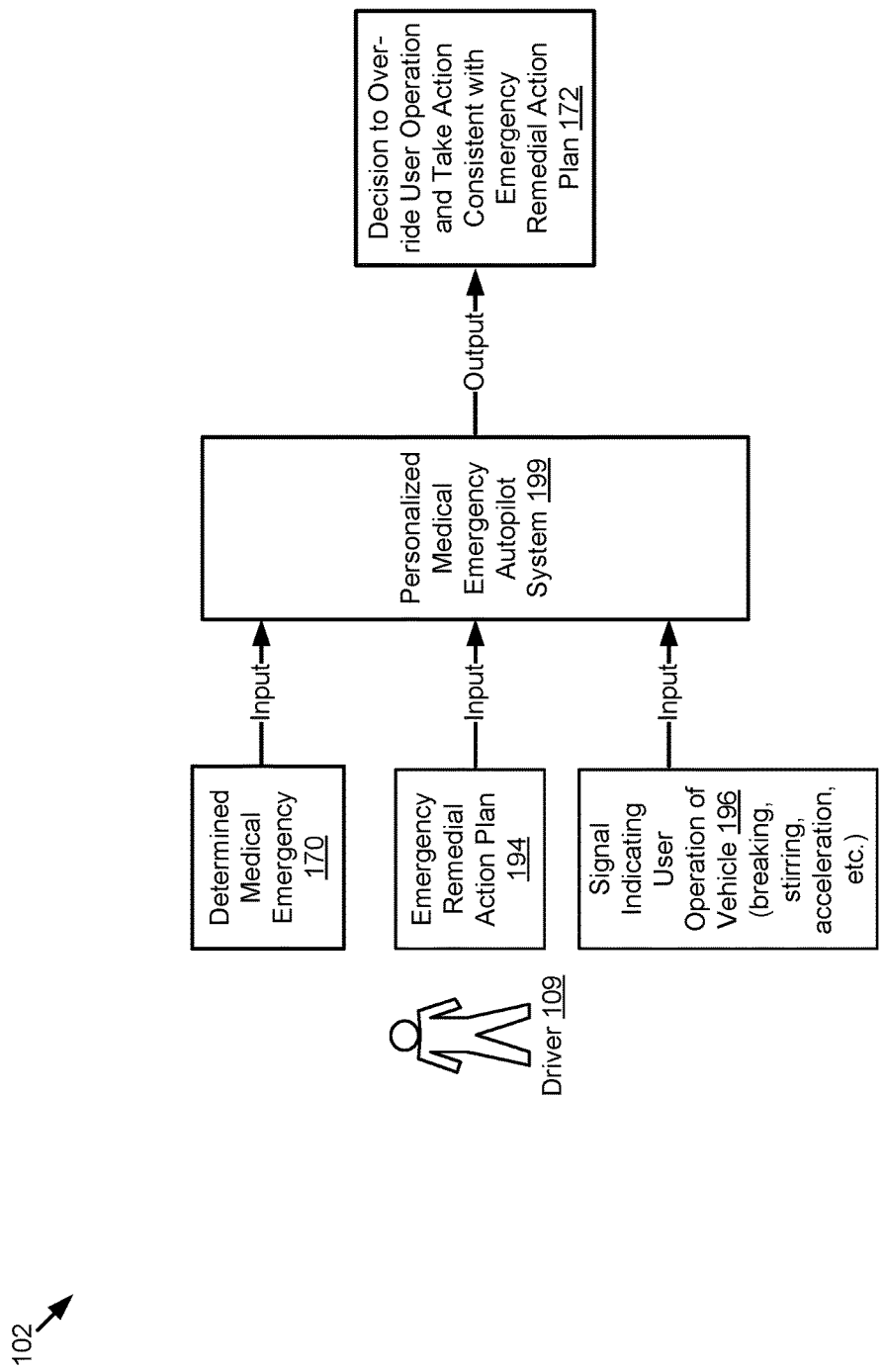
FIG. 1C is a block diagram illustrating process flow for a personalized medical emergency autopilot system according to some implementations.

Referring now to FIG. 1C, depicted is a block diagram illustrating process flow 102 for the personalized medical emergency autopilot system 199 according to some implementations.

The personalized medical emergency autopilot system 199 may receive inputs including one or more of the following: a determination of a medical emergency 170; the emergency remedial action plan 194; and a signal 196 indicating that the driver 109 is attempting to operating the vehicle subsequent to the determination of the medical emergency 170.

Responsive to these inputs, the personalized medical emergency autopilot system 199 may generate an output. The output may include a decision 172 to override the driver's ability to operate the vehicle 123 and to cause the vehicle 123 to take action consistent with the emergency remedial action plan 194 for the determined medical emergency 170.

Figure 2:
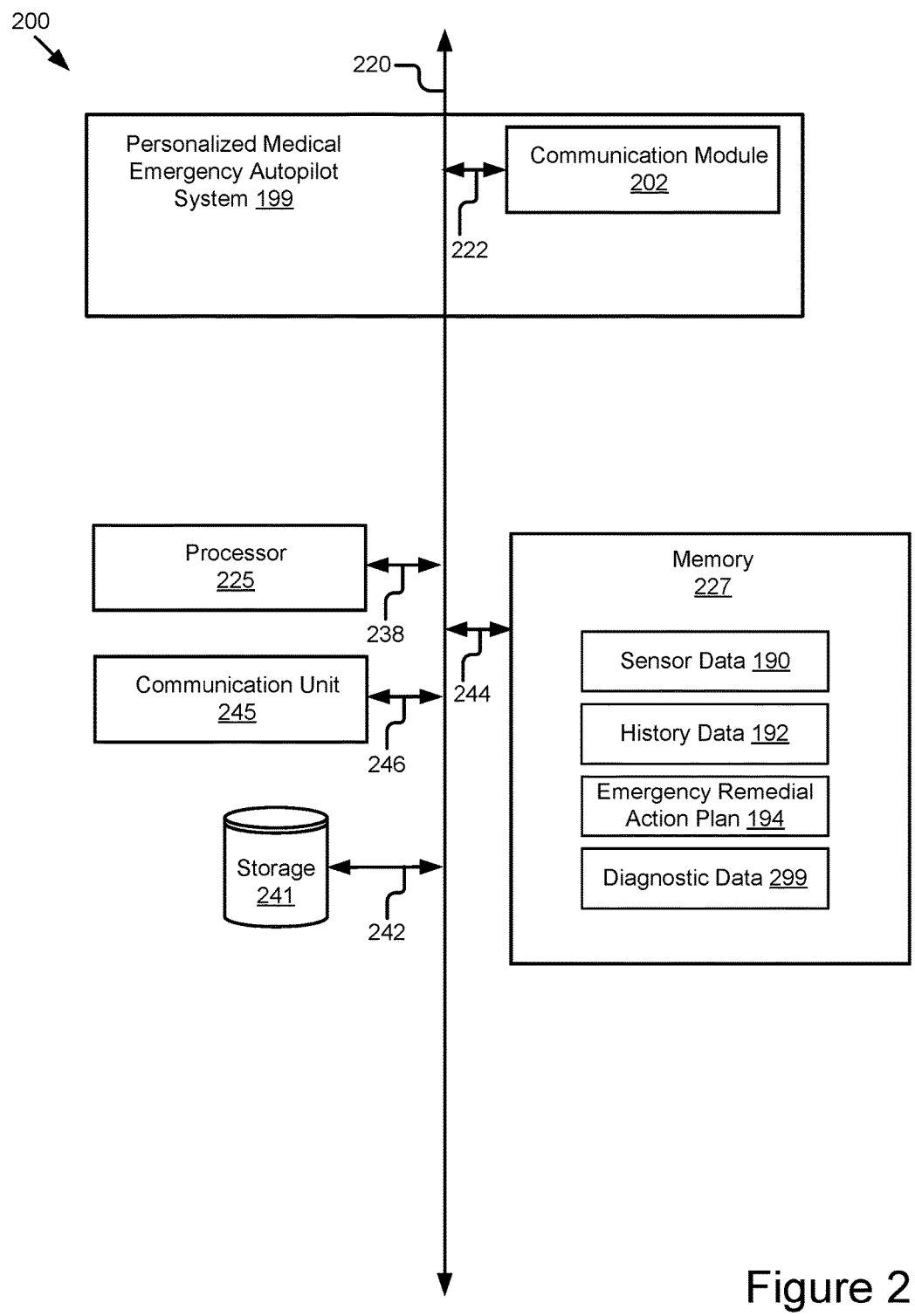
FIG. 2 is a block diagram illustrating an example computer system including a personalized medical emergency autopilot system according to some implementations.

Referring now to FIG. 2, depicted is a block diagram illustrating an example computer system 200 including a personalized medical emergency autopilot system 199 according to some implementations.

In some implementations, the computer system 200 may include a special-purpose computer system that is programmed to perform one or more steps of a method 300 described below with reference to FIGS. 3A and 3B.

In some implementations, the computer system 200 may include an onboard vehicle computer 150 of the vehicle 123. In some implementations, the computer system 200 may include an electronic control unit, head unit or some other processor-based computing device of the vehicle 123.

The computer system 200 may include one or more of the following elements according to some examples: the personalized medical emergency autopilot system 199; a processor 225; a communication unit 245; a storage 241; and a memory 227. In some implementations, the compute system 200 may be an element of the ADAS system 180. The components of the computer system 200 are communicatively coupled by a bus 220.

In the illustrated implementation, the processor 225 is communicatively coupled to the bus 220 via a signal line 238. The communication unit 245 is communicatively coupled to the bus 220 via a signal line 246. The storage 241 is communicatively coupled to the bus 220 via a signal line 242. The memory 227 is communicatively coupled to the bus 220 via a signal line 244.

The processor 225 includes an arithmetic logic unit, a microprocessor, a general purpose controller, or some other processor array to perform computations and provide electronic display signals to a display device. The processor 225 processes data signals and may include various computing architectures including a complex instruction set computer (CISC) architecture, a reduced instruction set computer (RISC) architecture, or an architecture implementing a combination of instruction sets. Although FIG. 2 includes a single processor 225, multiple processors may be included. The processor 225 may include a graphical processing unit. Other processors, operating systems, sensors, displays, and physical configurations may be possible.

The memory 227 stores instructions or data that may be executed by the processor 225. The instructions or data may include code for performing the techniques described herein. The memory 227 may be a dynamic random access memory (DRAM) device, a static random access memory (SRAM) device, flash memory, or some other memory device. In some implementations, the memory 227 also includes a non-volatile memory or similar permanent storage device and media including a hard disk drive, a floppy disk drive, a CD-ROM device, a DVD-ROM device, a DVD-RAM device, a DVD-RW device, a flash memory device, or some other mass storage device for storing information on a more permanent basis.

As illustrated in FIG. 2, the memory 227 stores one or more of the following elements: the sensor data 190; the history data 192; and the emergency remedial action plan 194. These elements were described above with reference to FIG. 1A, and so, their descriptions will not be repeated here. The memory 227 may also store diagnosis data 299.

The diagnosis data 299 may include any data necessary for the personalized medical emergency autopilot system 199 to identify a presence of a medical emergency based on one or more of the sensor data 190 and the history data 192. For example, the diagnosis data 299 may include data that describes different medical conditions and the symptoms (or physiological signals as described by the sensor data 190) that correspond to these different medical conditions for different demographic groups (as indicated, for example, by the history data 192) having different attributes (such as historical physiological readings, exercise frequency, smoker status, dietary habits, etc.).

Although not pictured in FIG. 2, in some implementations the memory 227 may store one or more keys or other data necessary to decrypt one or more of the sensor data 190 and the history data 192.

The communication unit 245 may include hardware that transmits and receives data to and from the network 105. In some implementations, the communication unit 245 includes a port for direct physical connection to the network 105 or to another communication channel. For example, the communication unit 245 includes a USB, SD, CAT-5, or similar port for wired communication with the network 105. In some implementations, the communication unit 245 includes a wireless transceiver for exchanging data with the network 105 or other communication channels using one or more wireless communication methods, including IEEE 802.11, IEEE 802.16, Bluetooth, or another suitable wireless communication method.

In some implementations, the communication unit 245 includes a port for direct physical connection to the network 105 or to another communication channel. For example, the communication unit 245 includes a USB, SD, CAT-5, or similar port for wired communication with the network 105.

In some implementations, the communication unit 245 includes a wireless transceiver for exchanging data with the network 105 or other communication channels using one or more wireless communication methods, including: IEEE 802.11; IEEE 802.16, Bluetooth; EN ISO 14906:2004 Electronic Fee Collection—Application interface EN 12253: 2004 Dedicated Short-Range Communication—Physical layer using microwave at 5.8 GHz (review); EN 12795:2002 Dedicated Short-Range Communication (DSRC)—DSRC Data link layer: Medium Access and Logical Link Control (review); EN 12834:2002 Dedicated Short-Range Communication—Application layer (review); EN 13372:2004 Dedicated Short-Range Communication (DSRC)—DSRC profiles for RTTT applications (review); the communication method described in U.S. patent application Ser. No. 14/471,387 filed on Aug. 28, 2014 and entitled "Full-Duplex Coordination System"; or another suitable wireless communication method.

In some implementations, the communication unit 245 may include a full-duplex coordination system as described in U.S. patent application Ser. No. 14/471,387 filed on Aug. 28, 2014 and entitled "Full-Duplex Coordination System."

In some implementations, the communication unit 245 includes a cellular communications transceiver for sending and receiving data over a cellular communications network including via short messaging service (SMS), multimedia messaging service (MMS), hypertext transfer protocol (HTTP), direct data connection, WAP, e-mail, or another suitable type of electronic communication. In some implementations, the communication unit 245 includes a wired port and a wireless transceiver. The communication unit 245 also provides other conventional connections to the network 105 for distribution of files or media objects using standard network protocols including TCP/IP, HTTP, HTTPS, and SMTP, millimeter wave, DSRC, etc.

The storage 241 can be a non-transitory storage medium that stores data for providing the functionality described herein. The storage 241 may be a dynamic random access memory (DRAM) device, a static random access memory (SRAM) device, flash memory, or some other memory devices. In some implementations, the storage 241 also includes a non-volatile memory or similar permanent storage device and media including a hard disk drive, a floppy disk drive, a CD-ROM device, a DVD-ROM device, a DVD-RAM device, a DVD-RW device, a flash memory device, or some other mass storage device for storing information on a more permanent basis.

In the illustrated implementation shown in FIG. 2, the personalized medical emergency autopilot system 199 includes a communication module 202.

The communication module 202 can be software including routines for handling communications between the personalized medical emergency autopilot system 199 and other components of the computer system 200. In some implementations, the communication module 202 can be a set of instructions executable by the processor 225 to provide the functionality described below for handling communications between the personalized medical emergency autopilot system 199 and other components of the computer system 200 or the operating environment 100. In some implementations, the communication module 202 can be stored in the memory 227 of the computer system 200 and can be accessible and executable by the processor 225. The communication module 202 may be adapted for cooperation and communication with the processor 225 and other components of the computer system 200 via signal line 222.

The communication module 202 sends and receives data, via the communication unit 245, to and from one or more elements of the computer system 200 or the network 105. For example, the communication module 202 receives, via the communication unit 245, one or more of the sensor data 190 and the history data 192.

In some implementations, the communication module 202 stores data in one or more of the storage 241 and the memory 227. For example, the communication module 202 data describing a decision made by the personalized medical emergency autopilot system 199 and stores data describing this decision in the memory 227.

In some implementations, the communication module 202 may handle communications between components of the computer system 200.

The personalized medical emergency autopilot system 199 can be software including routines for executing one or more steps of the method 300 described below with reference to FIGS. 3A and 3B. In some implementations, the personalized medical emergency autopilot system 199 can be stored in the memory 227 of the computer system 200 and can be accessible and executable by the processor 225.

In some implementations, the personalized medical emergency autopilot system 199 may analyze one or more of the sensor data 190 and the history data 192 to identify the presence of a medical emergency. The personalized medical emergency autopilot system 199 may remain inactive during normal driving conditions where a medical emergency is not indicated by the sensor data 190 or the history data 192. The personalized medical emergency autopilot system 199 may continuously receive updated sensor data 190 (and optionally history data 192) that describes real time or near real time physiological signal for the driver. The personalized medical emergency autopilot system 199 may continue to monitor this sensor data 190 relative to the diagnosis data 299 to identify a medical emergency. Until such an emergency is identified, the driver is able to operate the vehicle as they see fit. However, when the personalized medical emergency autopilot system 199 observes sudden changes in the physiological signals of the drivers in an abnormal way, the personalized medical emergency autopilot system 199 may override the drivers' control of the vehicle (e.g., driver's sudden braking, or sudden steering wheel rotation to the pedestrian road) so that the vehicle is operated in a way the conforms to the emergency remedial action plan 194 for the identified medical condition or medial emergency.

In some implementations, the history data 192 may be used by the personalized medical emergency autopilot system 199 to more accurately analyze the sensor data 190. For example, if the driver's average resting heart rate is 90 beats-per-minute, then a medical emergency may not be triggered unless the measured heart rate by the sensor data 190 corresponds to a medical emergency for a person of the same average resting heart rate, age, gender, height and weight who is experiencing a medical condition (e.g., heart attack). For example, based on this combination of history data 192 for the driver, the personalized medical emergency autopilot system 199 may understand that a medical emergency is only present if the resting heart rate is 120 beats-per-minute or greater. By comparison, technology that does not personalize the diagnosis of a medical condition based on the history data 192 may incorrectly declare a medical emergency if the heart rate is 100 beats-per-minute or greater, thereby resulting in a false diagnosis and a poor user experience. In this example, the personalized medical emergency autopilot system 199 may access the diagnosis data 299 to identify the provide the functionality described herein. For example, the diagnosis data 299 may include data that describes what heart rates correspond with a medical emergency for different combinations of history data 192 as described above. This example is only illustrative and is not intended to be exclusive.

In this way, the personalized medical emergency autopilot system 199 provides personalized diagnosis of medical emergencies for the driver based on the rich data available from portable medical devices that are now common.

The history data 192 may be an optional feature of the computer system 200.

Figure 3A:
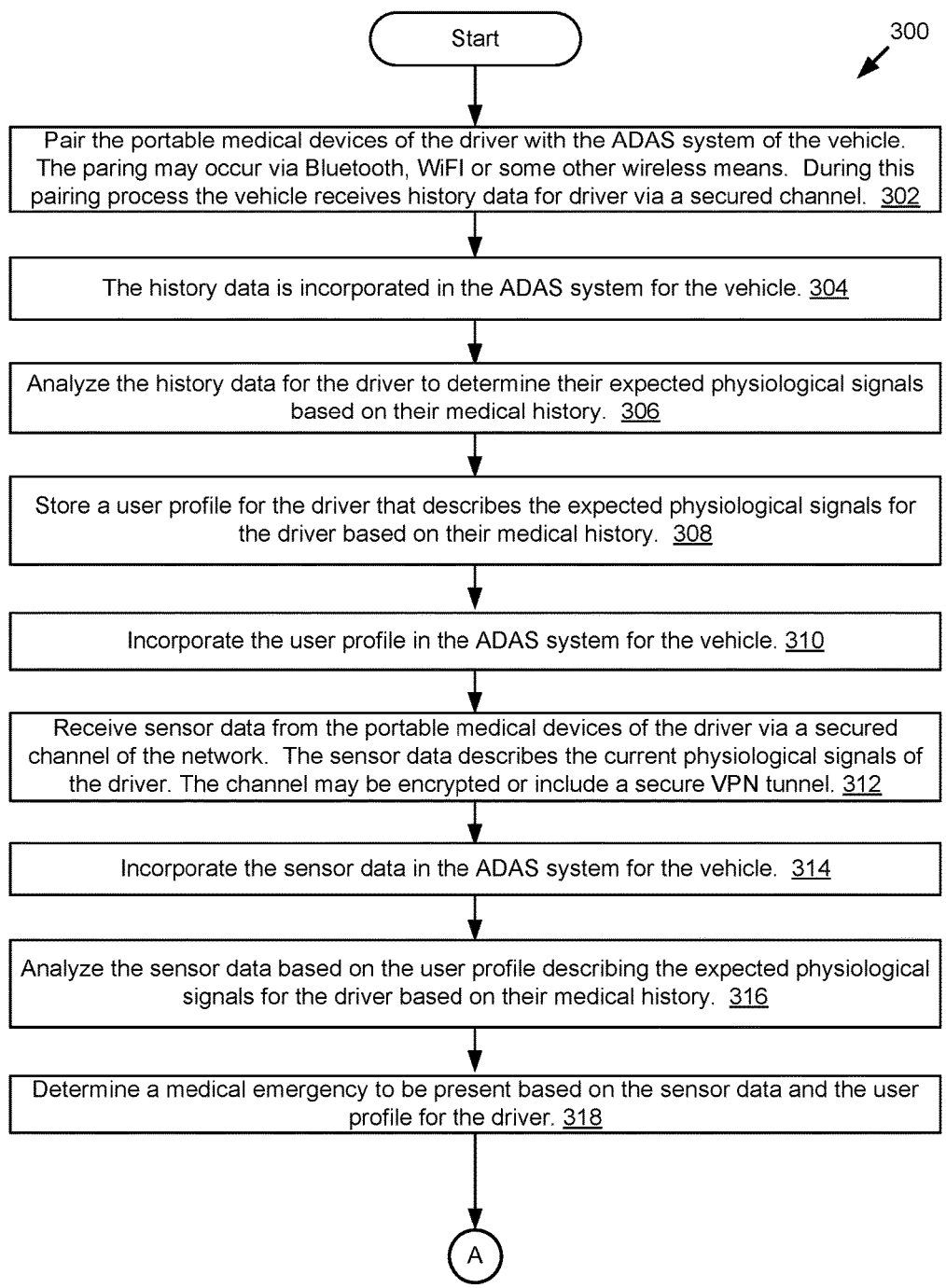
FIGS. 3A and 3B are a flowchart of an example method for a personalized medical emergency autopilot system to identify and respond to a medical emergency according to some implementations.
Figure 3B:
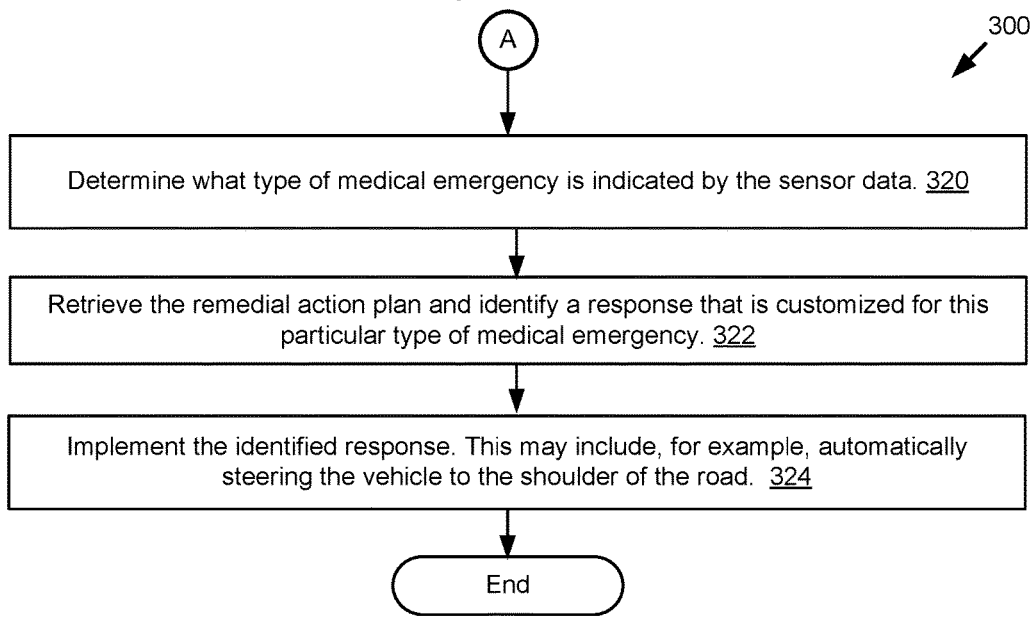

Referring now to FIGS. 3A and 3B, depicted is a flowchart of an example method 300 to identify and respond to a medical emergency according to some implementations.

At step 302, one or more portable medical devices of the driver may be paired with the ADAS system of the vehicle. The paring may occur via Bluetooth, Wi-Fi or some other wireless communication channel. During this pairing process the vehicle may receive the history data of the driver via a secured channel shared between the portable medical device and the communication unit of the vehicle.

At step 304, the history data is incorporated with the data used by the ADAS system to provide its functionality.

At step 306, the history data may be analyzed to determine the expected physiological signals for the driver based on the medical history described by the history data.

At step 308, a user profile for the driver may be stored in a memory. The user profile may be described by user profile data stored on the memory. The user profile for the driver may describe the expected physiological signals for the driver based on the medical history described by the history data. The user profile may be indexed by time or other variables so that the user profile describes the expected physiological signals for the driver based on variables such as time of day or day of week.

At step 310, the user profile for the driver (or the user profile data) may be incorporated into the data used by the ADAS system to provide its functionality.

At step 312, sensor data from one or more portable medical devices of the driver may be received. This sensor data may be received via a secured channel of the network. The sensor data may describe the current physiological signals of the driver. The channel may be encrypted or include a secure VPN tunnel. The sensor data may be received in real time or near real time relative to the time when the current physiological signals of the driver were recorded or measured. The sensor data may include a unique identifier associated with the driver that matches a unique identifier included in the sensor data to indicate which driver it describes. The unique identifier may also be stored in the user profile of the driver. The unique identifier may be shared with the one or more portable medical devices by the communication unit of the vehicle so that they may include this unique identifier in the sensor data shared with the vehicle.

At step 314, the sensor data may be incorporated into the data used by the ADAS system to provide its functionality.

At step 316, the sensor data may be analyzed based on the user profile of the driver describing the expected physiological signals for the driver based on their medical history.

At step 318, a medical emergency may be identified based on the sensor data and the user profile for the driver.

Referring now to FIG. 3B, at step 320 the diagnosis data may be retrieved. The diagnosis data may be analyzed with reference to the sensor data to identify a type of medical emergency indicated by the sensor data.

At step 322, the remedial action plan may be retrieved and analyzed based on the type of medical emergency indicated by the sensor data to identify a response that is customized for this particular type of medical emergency.

At step 324, the identified response may be implemented. For example, one or more ADAS systems of the vehicle may be instructed to control the operation of the vehicle so that the vehicle takes actions that are in accordance with the identified response.

Figure 4:
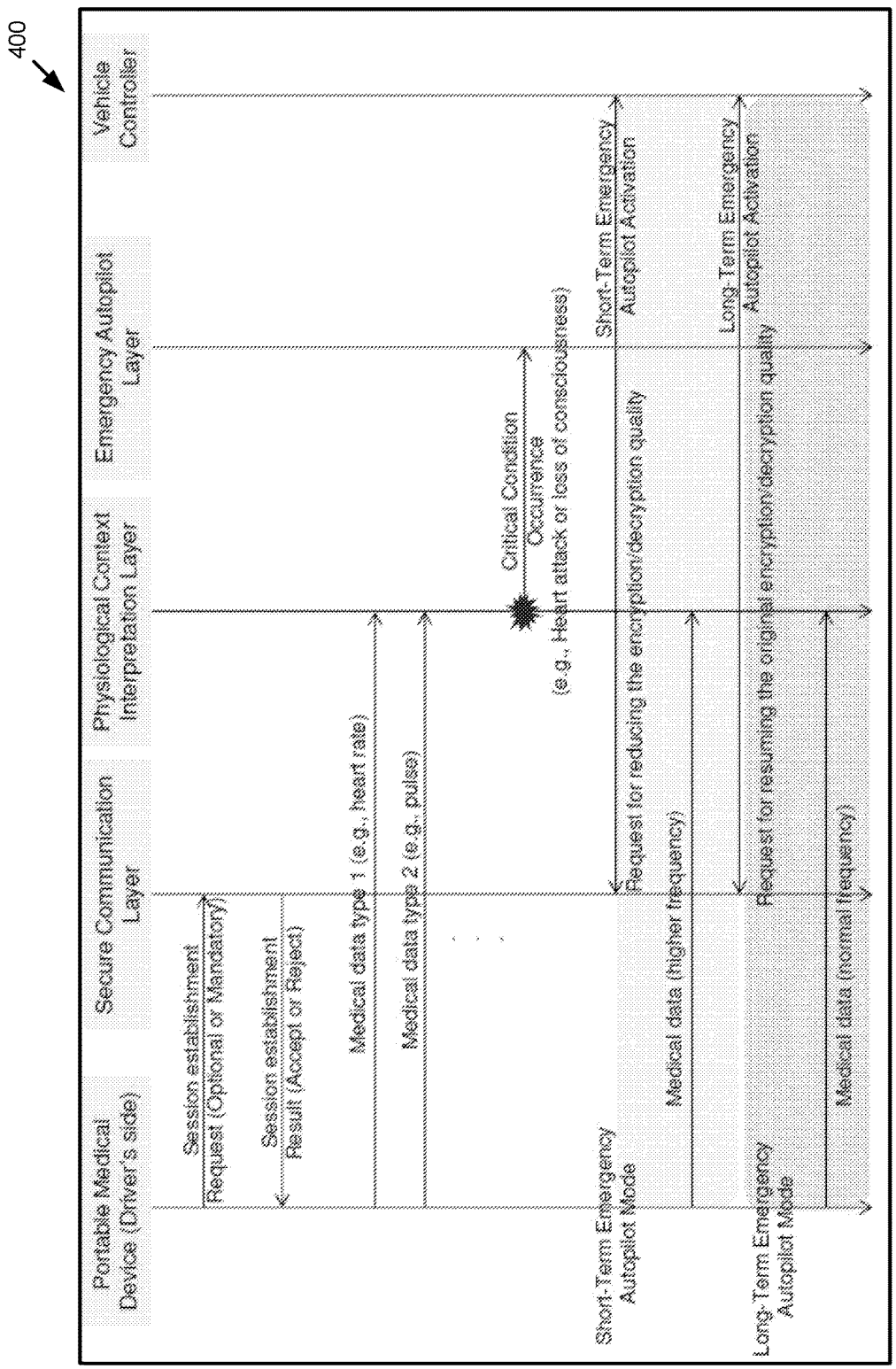
FIG. 4 is a block diagram illustrating an example of a layer architecture of a personalized medical emergency autopilot system according to some implementations.

Referring now to FIG. 4, depicted is a block diagram illustrating an example of a layer architecture 400 of a personalized medical emergency autopilot system according to some implementations.

The layer architecture 400 may include one or more of the following: (1) a secured communication layer with portable medical devices; (2) the physiological context interpretation layer; and (3) the emergency autopilot planning layer.

The secured communication layer may initiate a wireless communication session with one or more portable medical devices of the driver through an authentication mechanism. The authentication mechanism may include, for example, a Message Authentication Code (MAC), asymmetric cryptography (public/private keys) or any other authentication mechanism.

In some implementations, when driver starts driving, this secured communication session is established to receive one or more of the history data and the sensor data in real-time. This secure session can be optionally or forcefully established depending on the criticality of the drivers' medical conditions prescribed by a medical provider such as a doctor or nurse. The secured session may guarantee the confidentiality of one or more of the sensor data and the history data so that this information is not to exposed to non-authorized entities. However, establishing such secured session may diminish the performance of the computer system described in FIG. 2 due to the encryption/decryption overhead. Therefore, this layer may interact with the emergency autopilot layer in order to dynamically determine the right security level without compromising the performance of the emergency autopilot.

In some implementations, the physiological context interpretation layer may determine whether a driver is experiencing a medical emergency such that the emergency autopilot layer should be triggered. This decision may be made based on the sensor data received from the one or more portable medical devices through the communication session. This layer may maintain a personalized database of the thresholds of the physiological signals (e.g., heart rate, blood pressure) that indicate whether a driver is currently experiencing a medical emergency (e.g., the diagnosis data 299).

In some implementations, the emergency autopilot layer may be triggered by the physiological context interpretation layer. Once this layer is triggered, the personalized medical emergency autopilot system 199 may determine that the driver cannot make trustworthy or appropriate driving decision due to their medical emergency. Hence, the emergency autopilot layer may override the driver's ability to control the operation of the vehicle. Such overriding may be performed based on two strategies: (1) a short term strategy; and (2) a long term autopilot strategy.

In some implementations, the short term autopilot strategy may be configured to prevent accidents caused by the unconscious reaction of the driver that may follows the occurrence of the medical emergency. For example, the driver may unconsciously steer the wheel right in case of a sudden heart attack, which might result in hitting pedestrian. In this case, the personalized medical emergency autopilot system 199 may generate a counter force responsive to receiving a signal that the steering wheel is being turned. The personalized medical emergency autopilot system 199 may prevent the steering wheel control signal from being propagated to the engine motor so that the vehicle can avoid a collision in the short term.

In some implementations, a long term autopilot strategy may be configured to autonomously or remotely guide the vehicle so that the vehicle is driven to a safe place (e.g., an emergency room of a medical facility) to save the driver in case the driver cannot recover from the medical emergency within a certain period of time. For example: the vehicle may automatically find the nearest hospital, and drive the vehicle to the hospital; the vehicle may identify and park in a safe parking spot on the street; and the vehicle may inform one or more police stations or medical facilities about the location of the vehicle.

Referring now to FIG. 1A, one or more of the following devices may be a communication device: a vehicle 123; and one or more portable medical devices 103. Regarding U.S. patent application Ser. No. 14/471,387 filed on Aug. 28, 2014 and entitled "Full-Duplex Coordination System," which is herein incorporated by reference, in a half-duplex communication system, a first communication device currently transmitting data to a second communication device is not capable of simultaneously receiving data from the second communication device. If the second communication device has data to transmit to the first communication device, the second communication device needs to wait until the first communication device completes its data transmission. Only one communication device is allowed to transmit data at one time in the half-duplex communication system.

In a standard IEEE 802.11 Wireless Local Area Network (WLAN), communication devices may compete for access to a wireless channel based on the Carrier Sense Multiple Access with Collision Avoidance (CSMA/CA) Medium Access Control (MAC) protocol. The IEEE 802.11 MAC protocol requires that only one communication device may use the wireless channel to transmit data at one time. If two or more communication devices transmit data over the wireless channel at the same time, a collision occurs. As a result, only the communication device that currently gains access to the wireless channel may use the wireless channel to transmit data. Other communication devices having data to transmit need to monitor the wireless channel and may compete for access to the wireless channel when the wireless channel becomes idle again.

According to one innovative aspect of the subject matter described in this disclosure, the vehicle 123 and the portable medical device 103 and other communication devices as described above may include a full duplex coordination system for implementing full-duplex wireless communications among one another. The full duplex coordination system may include a processor and a memory storing instructions that, when executed, cause the full duplex coordination system to: create, at a first communication device (such as the vehicle 123), first data (such as a pairing request so that the vehicle may receive sensor data) to transmit to a second communication device (such as a portable medical device.); switch a half-duplex operation mode of the first communication device to a full-duplex operation mode to activate the full-duplex operation mode of the first communication device; transmit a first portion of the first data from the first communication device to the second communication device using a wireless channel; and transmit, in the full-duplex operation mode of the first communication device, a remaining portion of the first data to the second communication device while simultaneously receiving second data (such as any combination of the data stored on the memory 227) from the second communication device using the wireless channel.

According to another innovative aspect of the subject matter described in this disclosure, a full duplex coordination system for implementing full-duplex wireless communications includes a processor and a memory storing instructions that, when executed, cause the full duplex coordination system to: receive a first portion of first data from a first communication device via a wireless channel; determine that a second communication device is a single destination of the first data based on the first portion of the first data; determine that the second communication device has second data (such as any combination of the data stored on the memory 227) to transmit to the first communication device; determine that the first communication device has full-duplex communication capability; switch a half-duplex operation mode of the second communication device to a full-duplex operation mode to activate the full-duplex operation mode of the second communication device; and transmit, in the full-duplex operation mode of the second communication device, the second data to the first communication device while simultaneously receiving a remaining portion of the first data from the first communication device using the wireless channel.

In general, another innovative aspect of the subject matter described in this disclosure may be embodied in methods that include: creating, at a first communication device, first data to transmit to a second communication device; switching a half-duplex operation mode of the first communication device to a full-duplex operation mode to activate the full-duplex operation mode of the first communication device; transmitting a first portion of the first data from the first communication device to the second communication device using a wireless channel; and transmitting, in the full-duplex operation mode of the first communication device, a remaining portion of the first data to the second communication device while simultaneously receiving second data from the second communication device using the wireless channel.

Yet another innovative aspect of the subject matter described in this disclosure may be embodied in methods that include: receiving a first portion of first data from a first communication device via a wireless channel; determining that a second communication device is a single destination of the first data based on the first portion of the first data; determining that the second communication device has second data to transmit to the first communication device; determining that the first communication device has full-duplex communication capability; switching a half-duplex operation mode of the second communication device to a full-duplex operation mode to activate the full-duplex operation mode of the second communication device; and transmitting, in the full-duplex operation mode of the second communication device, the second data to the first communication device while simultaneously receiving a remaining portion of the first data from the first communication device using the wireless channel.

Another innovative aspect of the subject matter described in this disclosure may be embodied in methods that include: determining first data to transmit from a first communication device to a second communication device; and transmitting, from the first communication device that operates in a full-duplex operation mode, the first data to the second communication device while simultaneously receiving second data from the second communication device using a common wireless channel.

Another innovative aspect of the subject matter described in this disclosure may be embodied in methods that include: receiving, from a first communication device, first data at a second communication device via a wireless channel; determining second data to transmit from the second communication device to the first communication device responsive to receiving at least a portion of the first data; and transmitting, from the second communication device that operates in a full-duplex operation mode, the second data to the first communication device using the wireless channel while simultaneously receiving the first data from the first communication device.

Another innovative aspect of the subject matter described in this disclosure may be embodied in methods that include: determining, at a first communication device, first data to transmit to a second communication device; switching the first communication device from a half-duplex operation mode to a full-duplex operation mode; transmitting, in the full-duplex operation mode of the first communication device, the first data to the second communication device while simultaneously receiving second data from the second communication device using the wireless channel; and switching the full-duplex operation mode of the first communication device to the half-duplex operation mode responsive to a determination that transmission of the first data completes.

Another innovative aspect of the subject matter described in this disclosure may be embodied in methods that include: receiving, from a first communication device, first data at a second communication device via a wireless channel; determining that the second communication device has second data to transmit to the first communication device; switching the second communication device from a half-duplex operation mode to a full-duplex operation mode; transmitting, in the full-duplex operation mode of the second communication device, the second data to the first communication device while simultaneously receiving the first data from the first communication device using the wireless channel; and switching the full-duplex operation mode of the second communication device to the half-duplex operation mode responsive to a determination that transmission of the second data completes.

Other aspects include corresponding methods, systems, apparatus, and computer program products for these and other innovative aspects.

These and other implementations may each optionally include one or more of the following operations and features. For instance, the features include: the first data including a first packet and the first portion of the first data including a header portion of the first packet; the remaining portion of the first data including a payload portion and a trailer portion of the first packet; determining that the second communication device is a single destination of the first data; activating the full-duplex operation mode of the first communication device responsive to the second communication device being the single destination of the first data; the first communication device and the second communication device being communication devices in a wireless local area network; determining that the first communication device operates in a regulated spectrum where full-duplex communication capability is required; receiving device registry data associated with the first communication device; determining that the first communication device has full-duplex communication capability based on the device registry data; and determining that the first communication device has full-duplex communication capability based on a capability indication field in the first portion of the first data, the capability indication field including data describing whether the first communication device has full-duplex communication capability.

For instance, the operations include: determining that the wireless channel is idle; and accessing the wireless channel for data communication between the first communication device and the second communication device based on a channel access rule.

The disclosure is particularly advantageous in a number of respects. For example, the system described herein is capable of achieving a higher throughput and a faster communication speed using full-duplex communication technologies rather than using half-duplex communication technologies. The full-duplex communication may be implemented between vehicles or other communication devices that have full-duplex communication capability. In another example, the system coordinates communication between communication devices in a distributed way without using a central coordinator. The system determines a pair of communication devices and coordinates simultaneous transmission of data between the pair of communication devices so that the pair of communication devices may transmit data to each other simultaneously using the same wireless channel. Meanwhile, other communication devices may not transmit data over the wireless channel to avoid collision. The advantages of the system described herein are provided by way of example, and the system may have numerous other advantages.

The disclosure includes a system and method for implementing full-duplex wireless communications between communication devices. A full-duplex coordination system may include a processor and a memory storing instructions that, when executed, cause the full-duplex coordination system to: create, at a first communication device, first data to transmit to a second communication device; switch a half-duplex operation mode of the first communication device to a full-duplex operation mode to activate the full-duplex operation mode of the first communication device; transmit a first portion of the first data from the first communication device to the second communication device using a wireless channel; and transmit, in the full-duplex operation mode of the first communication device, a remaining portion of the first data to the second communication device while simultaneously receiving second data from the second communication device using the wireless channel.

In the above description, for purposes of explanation, numerous specific details are set forth in order to provide a thorough understanding of the specification. It will be apparent, however, to one skilled in the art that the disclosure can be practiced without these specific details. In some instances, structures and devices are shown in block diagram form in order to avoid obscuring the description. For example, the present implementations can be described above primarily with reference to user interfaces and particular hardware. However, the present implementations can apply to any type of computer system that can receive data and commands, and any peripheral devices providing services.

Reference in the specification to "some implementations" or "some instances" means that a particular feature, structure, or characteristic described in connection with the implementations or instances can be included in at least one implementation of the description. The appearances of the phrase "in some implementations" in various places in the specification are not necessarily all referring to the same implementations.

Some portions of the detailed descriptions that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms including "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission, or display devices.

The present implementations of the specification can also relate to an apparatus for performing the operations herein. This apparatus may be specially constructed for the required purposes, or it may include a general-purpose computer selectively activated or reconfigured by a computer program stored in the computer. Such a computer program may be stored in a computer-readable storage medium, including, but is not limited to, any type of disk including floppy disks, optical disks, CD-ROMs, and magnetic disks, read-only memories (ROMs), random access memories (RAMs), EPROMs, EEPROMs, magnetic or optical cards, flash memories including USB keys with non-volatile memory, or any type of media suitable for storing electronic instructions, each coupled to a computer system bus.

The specification can take the form of some entirely hardware implementations, some entirely software implementations or some implementations containing both hardware and software elements. In some preferred implementations, the specification is implemented in software, which includes, but is not limited to, firmware, resident software, microcode, etc.

Furthermore, the description can take the form of a computer program product accessible from a computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

A data processing system suitable for storing or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including, but not limited, to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem, and Ethernet cards are just a few of the currently available types of network adapters.

Finally, the algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the specification is not described with reference to any particular programming language. It will be appreciated that a variety of programming languages may be used to implement the teachings of the specification as described herein.

The foregoing description of the implementations of the specification has been presented for the purposes of illustration and description. It is not intended to be exhaustive or to limit the specification to the precise form disclosed. Many modifications and variations are possible in light of the above teaching. It is intended that the scope of the disclosure be limited not by this detailed description, but rather by the claims of this application. As will be understood by those familiar with the art, the specification may be embodied in other specific forms without departing from the spirit or essential characteristics thereof. Likewise, the particular naming and division of the modules, routines, features, attributes, methodologies, and other aspects are not mandatory or significant, and the mechanisms that implement the specification or its features may have different names, divisions, or formats. Furthermore, as will be apparent to one of ordinary skill in the relevant art, the modules, routines, features, attributes, methodologies, and other aspects of the disclosure can be implemented as software, hardware, firmware, or any combination of the three. Also, wherever a component, an example of which is a module, of the specification is implemented as software, the component can be implemented as a standalone program, as part of a larger program, as a plurality of separate programs, as a statically or dynamically linked library, as a kernel-loadable module, as a device driver, or in every and any other way known now or in the future to those of ordinary skill in the art of computer programming. Additionally, the disclosure is in no way limited to implementation in any specific programming language, or for any specific operating system or environment. Accordingly, the disclosure is intended to be illustrative, but not limiting, of the scope of the specification, which is set forth in the following claims.

What is claimed is:

1. A system comprising:
a vehicle communicatively coupled to a portable medical device of a driver via a wireless network;
wherein the vehicle includes an Advanced Driver Assistance System ("ADAS system");
wherein the ADAS system includes a personalized medical emergency autopilot system that is operable to receive sensor data of the driver via the wireless network, wherein the sensor data describes one or more current physiological signals describing the driver as recorded by one or more physiological sensors included in the portable medical device of the driver;
wherein the personalized medical emergency autopilot system is operable to analyze the one or more current physiological signals of the driver to identify a medical emergency for the driver;
wherein the personalized medical emergency autopilot system is operable to retrieve a remedial action plan and identify a response that is customized for the medical emergency for the driver; and
wherein the personalized medical emergency autopilot system is operable to respond based on the remedial action plan by overriding one or more vehicle control inputs provided by the driver subsequent to identifying the medical emergency so that the driver cannot control the operation of the vehicle during the medical emergency.

2. The system of claim 1, wherein analyzing the one or more current physiological signals of the driver to identify the medical emergency for the driver includes analyzing the sensor data based on a user profile that describes expected physiological signals for the driver based on a medical history of the driver.

3. The system of claim 1, wherein the response includes autonomously driving the vehicle to a specified location.

4. The system of claim 3, wherein the specified location is a medical facility and the response further includes wirelessly communicating with the medical facility via the wireless network to provide the medical facility with a wireless message that identifies the driver and the medical emergency.

5. The system of claim 4, wherein the wireless message further identifies one or more of an estimated time of arrival for the vehicle at the medical facility and a current geographic location of the vehicle.

6. The system of claim 3, wherein the specified location is parking location.

7. The system of claim 6, wherein the parking location includes one or more of a parking spot or a location in a breakdown lane.

8. The system of claim 6, wherein the response further includes wirelessly communicating with an emergency responder via the wireless network to provide the emergency responder with a wireless message that identifies the driver, the medical emergency and a geographic location of the parking location.

9. The system of claim 8, wherein the geographic location is accurate to within plus or minus substantially three meters.

10. A method comprising:
receiving, by a communication unit of a vehicle, a wireless message from a wireless network, wherein the wireless message includes sensor data describing one or more current physiological signals of a driver of the vehicle that are recorded by a portable medical device worn by the driver;
analyzing the one or more current physiological signals of the driver to identify a medical emergency for the driver;
identifying a response based on a remedial action plan that is customized for the medical emergency for the driver; and
overriding, by a personalized medical emergency autopilot system, based on the remedial action plan, one or more vehicle control inputs provided by the driver subsequent to identifying the medical emergency so that the driver cannot control the operation of the vehicle during the medical emergency.

11. The method of claim 10, wherein the one or more vehicle control inputs include steering the vehicle.

12. The method of claim 10, wherein the one or more vehicle control inputs include accelerating the vehicle.

13. The method of claim 10, wherein the one or more vehicle control inputs include braking the vehicle.

14. The method of claim 10, wherein overriding the one or more vehicle control inputs provided by the driver includes assigning a highest priority to one or more vehicle control inputs provided by an ADAS system of the vehicle so that the ADAS system may control the operation of the vehicle and the driver cannot control the operation of the vehicle.

15. The method of claim 10, wherein the wireless message is received via a secured communication channel and the method further comprises decrypting the wireless message.

16. The method of claim 10, wherein the sensor data is incorporated into an ADAS system of the vehicle so that the ADAS system has access to physiological signals of the driver.

17. A computer program product of a vehicle comprising a non-transitory memory storing computer-executable code that, when executed by a processor of the vehicle, causes the processor to:
receive a wireless message from a wireless network, wherein the wireless message includes sensor data describing one or more current physiological signals of a driver of the vehicle that are recorded by a portable medical device worn by the driver;
analyze the one or more current physiological signals of the driver to identify a medical emergency for the driver;
identify a response based on a remedial action plan that is customized for the medical emergency for the driver; and
override, based on the remedial action plan, one or more vehicle control inputs provided by the driver subsequent to identifying the medical emergency so that the driver cannot control the operation of the vehicle during the medical emergency.

18. The computer program product of claim 17, wherein the wireless message is transmitted to the wireless network by the portable medical device.

19. The computer program product of claim 17, wherein the wireless message is received in substantially real time relative to when the one or more current physiological signals are recorded by the portable medical device.

20. The computer program product of claim 17, wherein the one or more current physiological signals are directly recorded by the portable medical device and not inferred by the vehicle or the portable medical device.

\* \* \* \* \*